US007796040B2

(12) United States Patent
Mezhinsky et al.

(10) Patent No.: US 7,796,040 B2
(45) Date of Patent: Sep. 14, 2010

(54) SMART CONNECTOR SYSTEM FOR SURGICAL MACHINE

(75) Inventors: Victor Mezhinsky, Brea, CA (US); Argelio Olivera, Mission Viejo, CA (US); Kirk Todd, Yorba Linda, CA (US); Mark Hopkins, Mission Viejo, CA (US); Fang Wen, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 5 days.

(21) Appl. No.: 12/254,416

(22) Filed: Oct. 20, 2008

(65) Prior Publication Data

US 2009/0121838 A1    May 14, 2009

Related U.S. Application Data

(62) Division of application No. 11/491,068, filed on Jul. 21, 2006, now Pat. No. 7,443,296.

(51) Int. Cl.
*G08B 13/14* (2006.01)

(52) U.S. Cl. .............. 340/572.1; 340/572.4; 340/505; 340/539.1; 340/539.12; 340/825.69; 340/825.72; 340/10.1; 606/169; 606/170; 606/171

(58) Field of Classification Search ........... 340/572.1, 340/572.4, 505, 539.1, 539.12, 825.69, 825.72, 340/10.1; 235/383, 385; 600/300, 301; 606/1, 606/169, 170, 171
See application file for complete search history.

(56) References Cited

U.S. PATENT DOCUMENTS

| | | | |
|---|---|---|---|
| 4,623,776 A | 11/1986 | Buchroeder et al. | |
| 4,837,857 A | 6/1989 | Scheller et al. | |
| 5,052,725 A | 10/1991 | Meyer et al. | |
| 5,085,492 A | 2/1992 | Kelsoe et al. | |
| 5,104,158 A | 4/1992 | Meyer et al. | |
| 5,400,267 A | 3/1995 | Denen et al. | |
| 5,475,571 A | 12/1995 | Dassanayake | |

(Continued)

FOREIGN PATENT DOCUMENTS

EP    0740370 B1    10/1996

(Continued)

OTHER PUBLICATIONS

Appleby, "Drug makers using spy-novel strategies to thwart knockoffs", The Seattle Times, Aug. 19, 2003 (2 pages).

(Continued)

*Primary Examiner*—Hung T. Nguyen
(74) *Attorney, Agent, or Firm*—Darien Reddick

(57) ABSTRACT

A smart connector system includes a machine connector disposed on a face of a surgical machine, an illumination ring located on the face of the surgical machine and disposed around a periphery of the machine connector, an RFID reader antenna located in close proximity to the machine connector and the face of the surgical machine, and an accessory connector adapted to couple with the machine connector. The accessory connector has an RFID tag antenna and is capable of attaching a tool to the surgical machine. When the accessory connector is brought within close proximity to the machine connector, a communications connection is established between the RFID tag antenna and the RFID reader antenna.

20 Claims, 9 Drawing Sheets

U.S. PATENT DOCUMENTS

| | | | |
|---|---|---|---|
| 5,494,074 A | 2/1996 | Ramacier, Jr. et al. |
| 5,554,049 A | 9/1996 | Reynolds |
| 5,911,403 A | 6/1999 | deCler et al. |
| 5,975,489 A | 11/1999 | deCler et al. |
| 6,024,124 A | 2/2000 | Braun et al. |
| 6,082,401 A | 7/2000 | Braun et al. |
| 6,161,578 A | 12/2000 | Braun et al. |
| 6,172,609 B1 | 1/2001 | Lu et al. |
| 6,222,193 B1 | 4/2001 | Thurston et al. |
| 6,231,089 B1 | 5/2001 | DeCler et al. |
| 6,273,338 B1 | 8/2001 | White |
| 6,319,031 B1 | 11/2001 | Greenstein |
| 6,382,593 B1 | 5/2002 | deCler et al. |
| 6,430,371 B1 | 8/2002 | Cho |
| 6,574,166 B2 | 6/2003 | Niemiec |
| 6,626,419 B2 | 9/2003 | deCler et al. |
| 6,649,829 B2 | 11/2003 | Garber et al. |
| 6,705,591 B2 | 3/2004 | deCler |
| 6,848,602 B2 | 2/2005 | deCler et al. |
| 6,861,954 B2 | 3/2005 | Levin |
| 6,897,374 B2 | 5/2005 | Garber et al. |
| 6,899,476 B1 | 5/2005 | Barrus et al. |
| 6,902,144 B2 | 6/2005 | deCler |
| 6,903,656 B1 | 6/2005 | Lee |
| 6,916,007 B2 | 7/2005 | deCler et al. |
| 6,917,291 B2 | 7/2005 | Allen |
| 6,978,800 B2 | 12/2005 | deCler et al. |
| 7,273,483 B2 * | 9/2007 | Wiener et al. ............... 606/169 |
| 7,443,296 B2 | 10/2008 | Mezhinsky et al. |
| 7,484,769 B2 | 2/2009 | Domash et al. |
| 7,568,619 B2 | 8/2009 | Todd et al. |
| 2001/0020148 A1 | 9/2001 | Sasse et al. |
| 2002/0017996 A1 | 2/2002 | Niemiec |
| 2002/0032435 A1 | 3/2002 | Levin |
| 2002/0143320 A1 | 10/2002 | Levin |
| 2003/0127508 A1 | 7/2003 | Jones |
| 2003/0178488 A1 | 9/2003 | Southard |
| 2003/0178489 A1 | 9/2003 | Boukhny et al. |
| 2004/0114879 A1 | 6/2004 | Hiereth et al. |
| 2004/0220602 A1 | 11/2004 | Deng et al. |
| 2006/0043177 A1 * | 3/2006 | Nycz et al. ............... 235/385 |
| 2006/0129140 A1 | 6/2006 | Todd et al. |
| 2007/0027459 A1 | 2/2007 | Horvath et al. |
| 2008/0030343 A1 | 2/2008 | Raybuck et al. |
| 2008/0054073 A1 | 3/2008 | Charles et al. |
| 2008/0262654 A1 * | 10/2008 | Omori et al. ............... 700/245 |

FOREIGN PATENT DOCUMENTS

| | | |
|---|---|---|
| EP | 1199046 A2 | 4/2002 |
| EP | 1410766 A1 | 4/2004 |
| WO | 0114912 A1 | 3/2001 |
| WO | 02099774 A2 | 12/2002 |
| WO | 03026558 A2 | 4/2003 |
| WO | 2006036600 A1 | 4/2006 |

OTHER PUBLICATIONS

Baschet-Vernet, "Smart packages may help control prescriptions", Pharmpack Europe, Nov. 2002(5) (3 pages).

ATMEL Corporation, "Electronic Immobilizers for the Automotive Industry", U2270B, Rev. 2661A-RFID Jun. 2003 (18 pages).

Lee, Dr. Youbok, "MCRF, 355/360 Applications", Microchip Technology, Inc., AN707, 1999:DS00707A (5 pages).

* cited by examiner

US 7,796,040 B2

SMART CONNECTOR SYSTEM FOR SURGICAL MACHINE

This application is a division of U.S. Ser. No. 11/491,068 filed on Jul. 21, 2006, now U.S. Pat. No. 7,443,296.

FIELD OF THE INVENTION

The present invention relates to surgical machines and more particularly to an RFID and ring illumination system for facilitating the connection of accessories to a surgical machine.

BACKGROUND OF THE INVENTION

Many operations performed today involve the use of complex surgical machines. Computerized equipment is often used by surgeons in the operating room (OR) to conduct surgery. These machines monitor and implement various stages of an operation. For example, in ophthalmic surgery, computerized machines and associated tools are used by a surgeon to perform cataract removal and lens replacement. Other machines are used to perform retinal surgery. These machines allow the surgeon to proceed through the steps of an operation.

Most surgical machines are designed to work with various tools. In ophthalmic surgery, these tools include probes, scissors, hand pieces, illuminators, lasers, and consumables. These tools are designed to connect to the front console of the surgical machine. For example, a surgeon performing retinal surgery may attach a small pair of pneumatically driven scissors to the machine. The scissors, in the form of a hand piece, are connected to a pneumatic connector on the front console of the machine with a cable. The cable provides the pneumatic power required to operate the scissors. One end of the cable is attached to the scissors while the other end has a connector designed to couple with the pneumatic connector on the front console of the machine.

Typically, the front console of the machine has a number of connectors designed to connect with and power various tools. For example, one connector may be designed to provide pneumatic power to a tool while another connector may be designed to provide electric power to a different tool. In addition, a single pneumatic connector on the front console may be designed to interface with a number of different pneumatically-driven tools. Each tool that is plugged into the pneumatic connector will perform its intended function. One tool may be a pair of scissors used to cut tissue. Another tool may be a type of probe or a drug delivery device. Since each of these tools is designed to connect with the pneumatic connector on the console of the surgical machine, each is driven by the pneumatic power supplied by the machine.

A problem can arise during surgery when the wrong tool is connected to the machine. In such a case, the tool operates normally, but the wrong procedure is performed on the patient. For example, a surgeon may mistakenly attach a pair of pneumatically-driven scissors to a machine when he intends to attach a pneumatically-driven drug delivery device. The scissors will perform their intended function of cutting tissue. Since the surgeon intended to deliver a dosage of a drug, however, the unwanted cutting performed by the scissors can injure the patient.

As another example, there may be two different types of cutting tools. Each one may interface with the same connector on the front console of the machine. Using the wrong cutting tool can inflict unintended harm on the patient. Further, there may be two different types of electrically-driven tools, such as an illuminator and a laser. Using a laser when an illuminator is required can harm the patient. In sum, error on the part of the surgeon in using the wrong tool or the wrong type of tool can unintentionally injure a patient during an operation.

Further confusion can occur because of the labeling present on the front of a surgical machine. In conventional surgical machines, the connectors on the front console are passively labeled. A pneumatic connector designed to work with several different tools may be labeled with a single icon, symbol or LED. This passive labeling may identify the type of connector or that power is being delivered through the connector, but such labeling is ineffective at preventing surgeon error.

In order to address this problem, some conventional surgical machines employ a set of different connectors for a set of different tools. In this manner, each tool is designed to mate with its own connector. However, this configuration of numerous different connectors can be confusing to the surgeon and adds additional expense and complexity to the design of the surgical machine. Moreover, different versions of the same type of tool may interface with a single one of the connectors on the front console of the machine. For example, two different types of scissors may be adapted to fit the same pneumatic connector on the front console of the machine. Using the wrong type of scissors might harm the patient.

Machines with conventional connectors also do not allow the collection of data from the tool. Since the physical connector on the front of the machine is often dumb, it cannot tell which tool is connected to it. Conventional connectors are adapted simply to provide the correct electric or pneumatic power to a tool. These connectors cannot discern what type of tool is connected to them. They also cannot identify a particular tool, how many times a particular tool was used, and other information about how the tool is operating or even if it is operating properly.

A smart connector system for a surgical machine is needed to address these problems.

SUMMARY OF THE INVENTION

In one embodiment consistent with the principles of the present invention, the present invention is a smart connector system for a surgical machine having a machine connector disposed on a face of a surgical machine, an illumination ring located on the face of the surgical machine and disposed around a periphery of the machine connector, an RFID reader antenna located in close proximity to the machine connector and the face of the surgical machine, and an accessory connector adapted to couple with the machine connector. The accessory connector has an RFID tag antenna and is capable of attaching a tool to the surgical machine. When the accessory connector is brought within close proximity to the machine connector, a communications connection is established between the RFID tag antenna and the RFID reader antenna.

In another embodiment consistent with the principles of the present invention, the present invention is a ring illumination system including a surgical machine having a main surgical console and a display. The system also has a machine connector disposed on a face of the main surgical console. The machine connector is adapted to provide power to a surgical tool. The system also has an illumination ring located on the face of the main surgical console and disposed around a periphery of the receiving connector. The illumination ring has a light source and a light diffusive and refractive element. The system also has an RFID reader including an RFID reader antenna located in close proximity to the machine connector and the face of the main surgical console. The system also has an accessory connector adapted to couple with the machine connector. The accessory connector has an RFID tag and is configured to attach the surgical tool to the main surgical console. When the accessory connector is brought within close proximity to the machine connector, a communications connection is established between the RFID tag and the RFID reader.

In another embodiment consistent with the principles of the present invention, the present invention is a method of ensuring that a surgical tool is used safely with a surgical machine. The method includes the steps of establishing a communications connection between the surgical machine and the surgical tool, reading an identification datum from the surgical tool, based on the identification datum, determining if the surgical tool can safely be used with the surgical machine, and providing power to the surgical tool only if it is safe to do so.

In another embodiment consistent with the principles of the present invention, the present invention is method of ensuring the safe use of a surgical tool with a surgical machine. The method includes the steps of establishing a communications connection between the surgical machine and the surgical tool, reading an identification datum from the surgical tool, reading a use datum from the surgical tool, based on the identification datum and the use datum, determining if the surgical tool can safely be used with the surgical machine, and disabling the surgical tool if it cannot be safely used.

In another embodiment consistent with the principles of the present invention, the present invention is a method of gathering information from a surgical tool. The method has the steps of establishing a communications connection between the surgical machine and the surgical tool, reading an identification datum and a use datum from the surgical tool, and recording the use datum in a memory.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
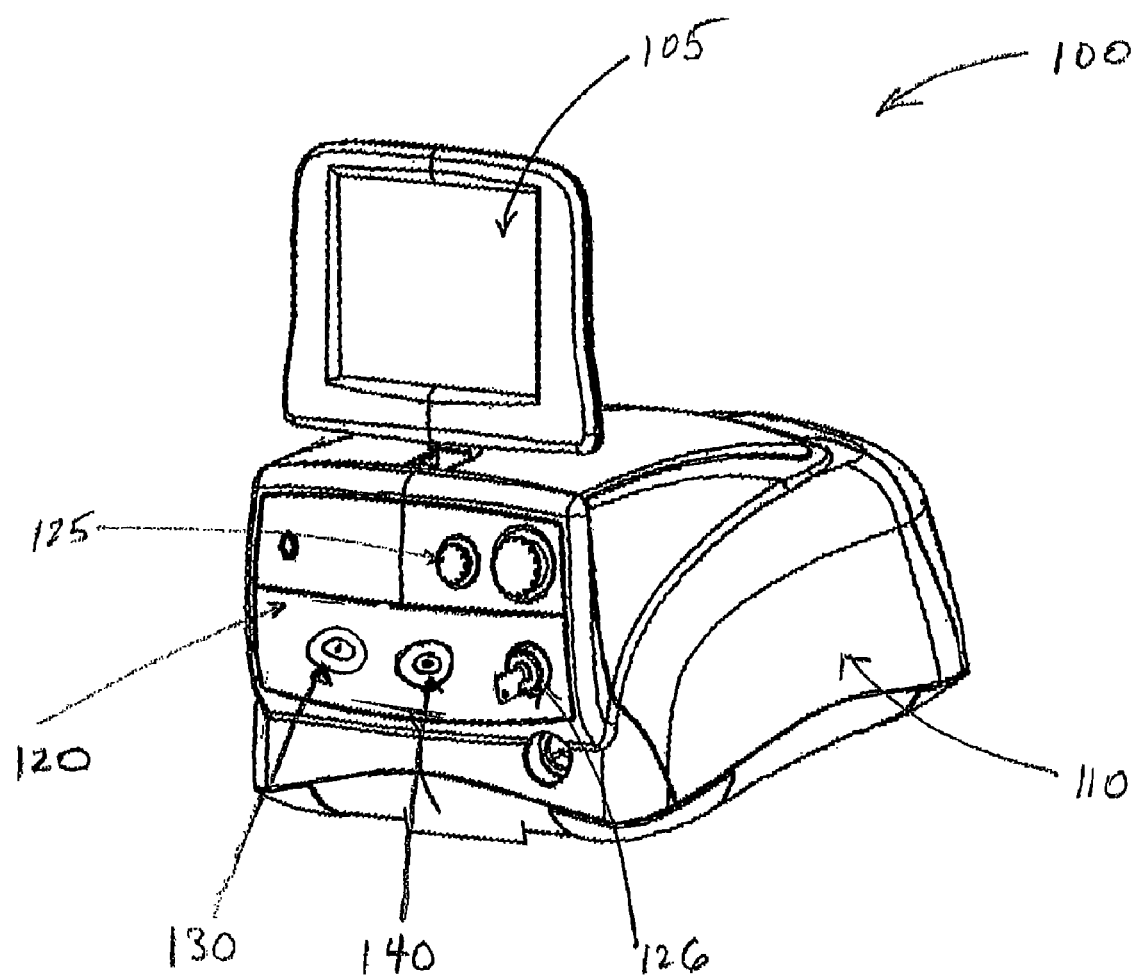
FIG. 1 is a perspective view of a surgical machine with an RFID illumination ring system according to an embodiment of the present invention.

FIG. 1 is a perspective view of a surgical machine 100 with an RFID illumination ring system according to an embodiment of the present invention. In FIG. 1, surgical machine 100 has a display 105 and a main surgical console 110. Information about the operation and status of surgical machine 100 is displayed on display 105. Main surgical console 110 contains the circuitry (not shown) to operate surgical machine 100. Main surgical console has a front panel 120 located on the front of surgical machine 100. Various controls, such as control knob 125 and key lock 126, are located on front panel 120. In addition, an electrical connector and illumination ring 130 and a pneumatic connector and illumination ring 140 are located on front panel 120. While the location of the controls 125, 126 and the connectors and illumination rings 130, 140 are shown on front panel 120, their location can be anywhere on main surgical console 110, display 105, or other peripheral (not shown). Surgical machine 100 also contains and RFID reader (not shown). A typical RFID reader includes an RFID antenna, transceiver, microprocessor, power supply, and signal conditioning circuitry.

Figure 2:
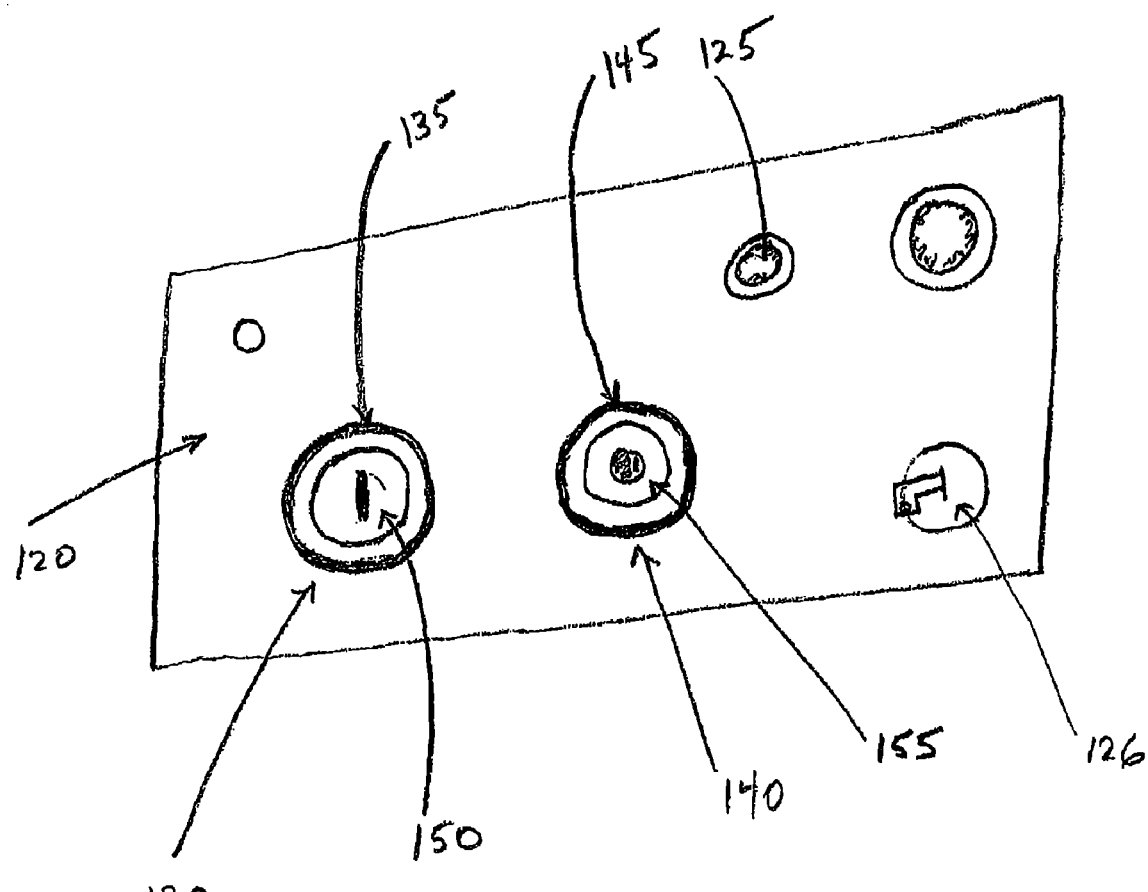
FIG. 2 is a perspective view of a front panel of a surgical machine with an RFID illumination ring system according to an embodiment of the present invention.

FIG. 2 shows a more detailed view of the front panel 120 depicted in FIG. 1. Front panel 120 holds controls, such as control knob 125 and key lock 126. Front panel 120 also has two connectors with illumination rings 130, 140. Electrical connector with illumination ring 130 has an illumination ring 135 and an electrical connector 150. Illumination ring 135 is located around the periphery of electrical connector 150. Pneumatic connector with illumination ring 140 has an illumination ring 145 and a pneumatic connector 155. Illumination ring 145 is located around the periphery of pneumatic connector 155.

Electrical connector 150 is adapted to receive a mating connector from an electrically-powered accessory, such as a tool. When connected to an electrically-powered accessory, electrical connector 150 provides power to that accessory. Likewise, pneumatic connector 155 is adapted to receive a mating connector from a pneumatically-powered accessory, such as a tool. When connected to a pneumatically-powered accessory, pneumatic connector 155 provides power to that accessory.

The illumination rings 135, 145 are designed to display visible light in a ring-like configuration. In this manner, a surgeon operating the surgical machine 100 can see when an illumination ring is lit. Illumination rings 135, 145 are designed to display different colors indicating different modes of operation or statuses of the surgical machine 100 as discussed in further detail below. While shown as a continuous ring, illumination rings 135, 145 may take on numerous different configurations without departing from the scope and spirit of this invention. For example, illumination rings 135, 145 may be in the shape of a square, triangle, or any other polygon. In addition, the light produced by illumination rings 135, 145 need not be continuous as shown. While a continuous ring of light is generally more useful and aesthetically pleasing, a broken ring of light can also be used as can flashing or pulsating light.

Figure 3:
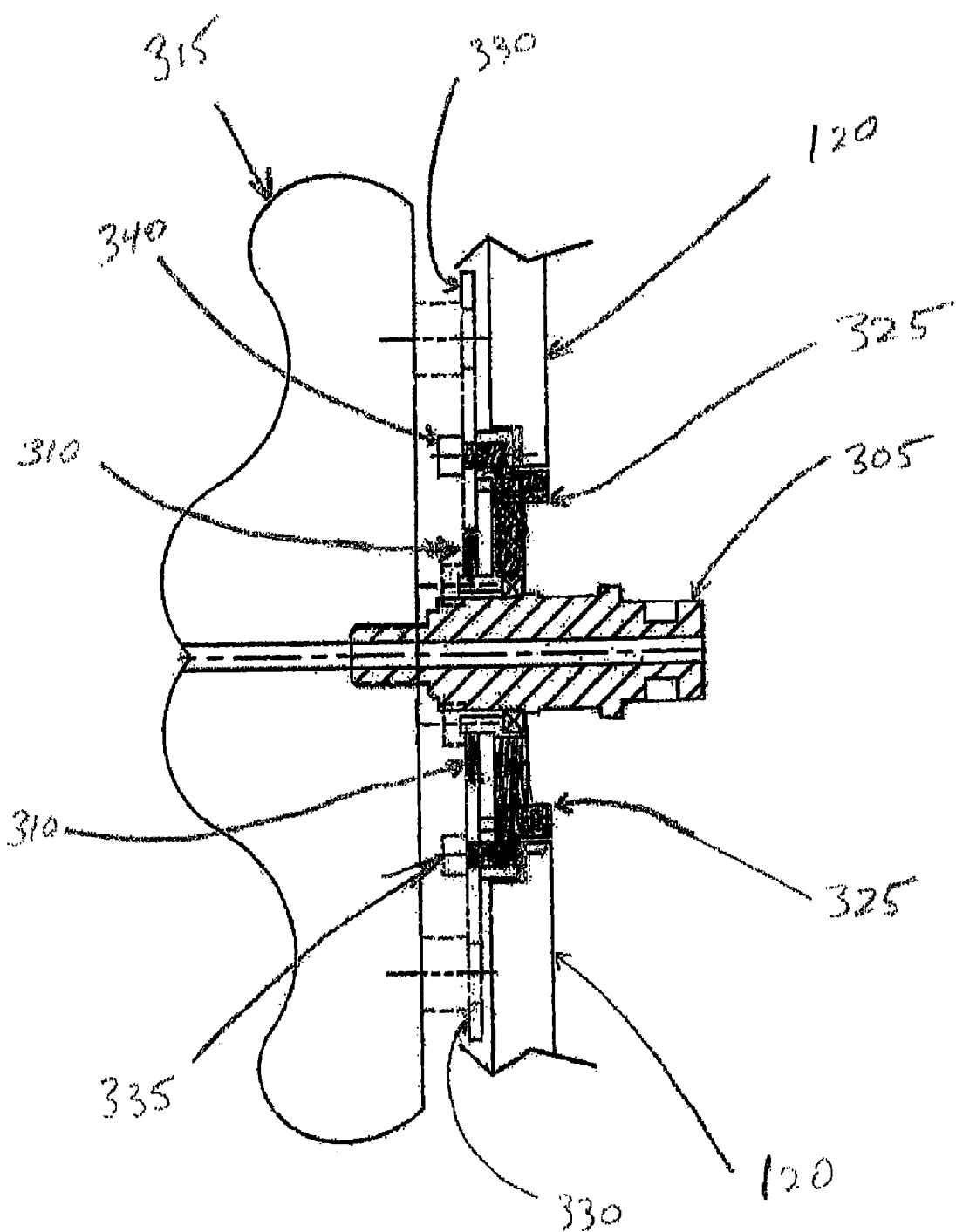
FIG. 3 is an exploded view of a connector and illumination ring on the front panel of a surgical machine with an RFID illumination ring system according to an embodiment of the present invention.

FIG. 3 is an exploded side view of a connector and illumination ring located on front panel 120 of surgical machine 100. In FIG. 3, male connector 305 is mounted onto manifold 315 of surgical machine 100. Manifold 315 is located behind and attached to front panel 120 of surgical machine 100. Printed circuit board (PCB) 330 is located between manifold 315 and front panel 120. Male connector protrudes through PCB 330 and front panel 120 to allow connection with a female connector on a tool (not shown). Light emitting diodes (LEDs) 335 and 340 are mounted on the side of PCB 330 that faces the manifold 315. In other words, LEDs 335 and 340 are mounted on the side of PCB 330 that does not face front panel 120. RFID reader antenna 310 is also located on or integrated into PCB 330. Lens 325 is located in front of PCB 330 and in a plane substantially parallel with front panel 120. The front face of lens 325 is visible when looking at the front panel 120.

In FIG. 3, an illumination ring is implemented with LEDs 335, 340 and lens 325. Light from LEDs 335, 340 passes through holes in the PCB 330 (not shown) and is refracted and diffused by lens 325. A ring of visible light is observed when looking at the lens 325 on front panel 120. In order to produce a uniform ring of light, lens 325 refracts and diffuses the light produced by LEDs 335, 340. In this manner, an illumination ring is located around the periphery of male connector 305.

Figure 4:
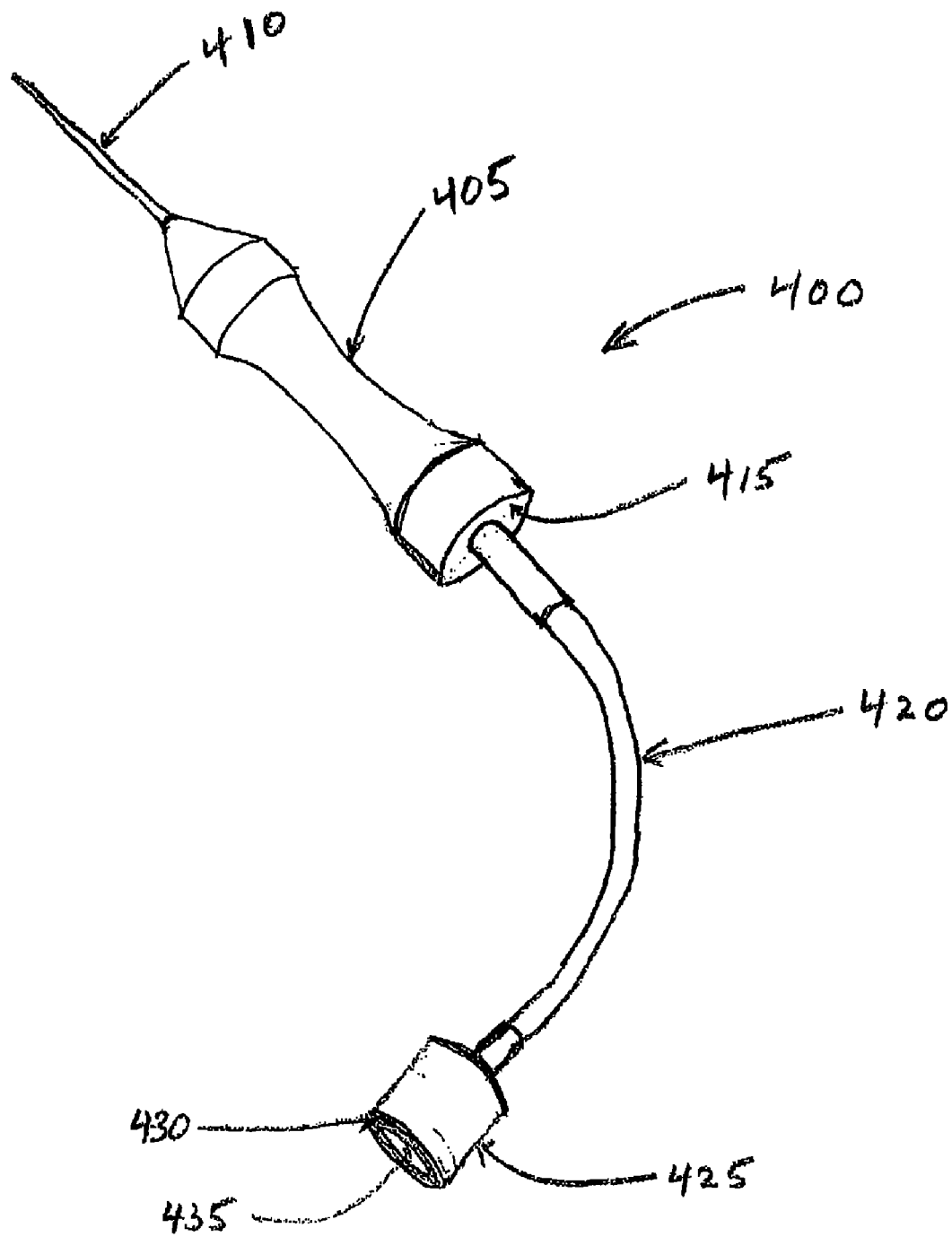
FIG. 4 is a perspective view of a tool containing an RFID tag for use with a surgical machine with an RFID illumination ring system according to an embodiment of the present invention.

FIG. 4 is a perspective view of a tool containing an RFID tag for use with surgical machine 100. Tool 400 has a hand piece 405, cable 420, and a female connector 425. Hand piece 405 has a working tip 410 which can be any type of device used in surgery. For example working tip 410 may be a small pair of pneumatic scissors designed to cut ocular tissue or a drug delivery device designed to place a quantity of drug in the posterior of an eye. Cable 415 connects to hand piece 405 on surface 415. Cable 420 extends from surface 415 of hand piece 405 to female connector 425. Cable 420 attaches to female connector 425 on a surface (not shown) opposite receiving cavity 435. In one configuration, cable 420 is adapted to provide electrical power to hand piece 405 and working tip 410. In another configuration, cable 420 is adapted to provide pneumatic power to hand piece 405 and working tip 410. Cable 420 may help to control hand piece 405 and working tip 410, such as by varying levels of power. In this manner, cable 420 could be used to both power and control hand piece 405 and working tip 410.

Female connector 425 has a generally cylindrical shape. Female connector 425 has a receiving cavity 435 adapted to fit male connector 305. In this manner, the receiving cavity 435 on connector 425 has a female configuration, and male connector 305 has a male configuration. When connected, surgical machine delivers 100 delivers power to tool 400. While female connector 425 is shown with a female configuration, it is understood that any suitable configuration can be used. For example, female connector 425 can be reconfigured to have a male configuration, and male connector 305 can be reconfigured to have a female configuration.

Female connector 425 also has an RFID tag 430 disposed on a surface around receiving cavity 435. The location of RFID tag 430 is designed to place the tag close to front panel 120 when female connector 425 is connected to male connector 305. In this manner, the antenna of the RFID tag 430 is placed in close proximity to the reader antenna 310. The antenna of RFID tag 430 also has a circular configuration similar to the circular configuration of reader antenna 310. While shown as having a circular configuration, any antenna configuration can be used without departing from the scope of the present invention.

Figure 5:
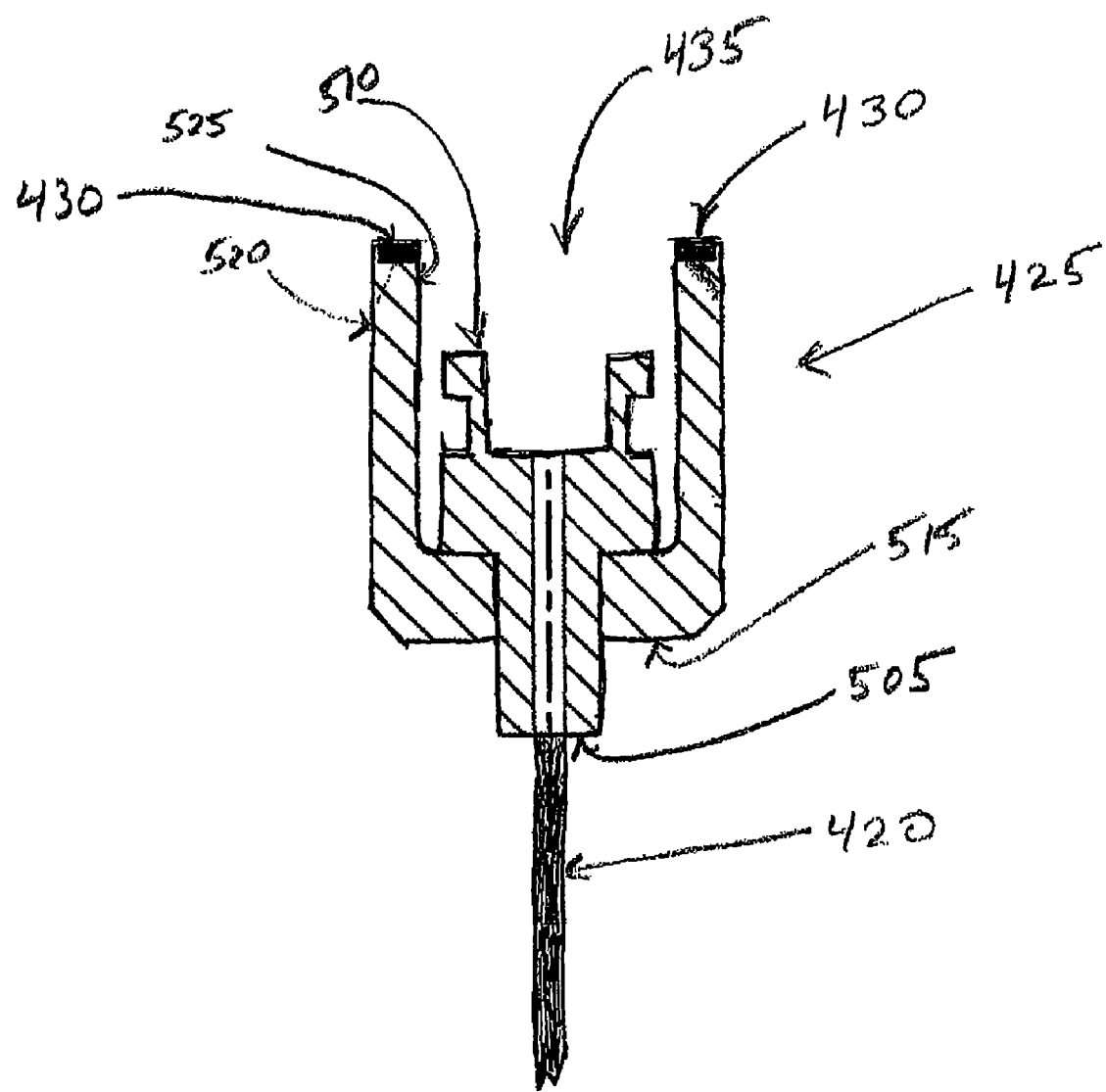
FIG. 5 is an exploded cross-section view of a connector on a tool for use with a surgical machine with an RFID illumination ring system according to an embodiment of the present invention.

FIG. 5 is an exploded cross-section view of the female connector 425 depicted in FIG. 4. Female connector 425 has a generally cylindrical shape. Surface 505 and surface 515 are generally parallel. Cable 420 extends from surface 505 outward toward hand piece 405. Cable 420 also extends inward from surface 505 to enable the necessary internal connections with female connector 425. In this manner, power can be delivered from surgical machine 100 through male connector 305 to female connector 425 through cable 420 and to hand piece 405 and working tip 410.

RFID tag 430 is arranged circularly around receiving cavity 435 on a surface opposite surface 515. Alternatively, RFID tag can be disposed on exterior surface 520 or interior surface 525 or other location near receiving cavity 435. Female connector 425 is also shown with member 510 adapted to connect with male connector 305.

Figure 6:
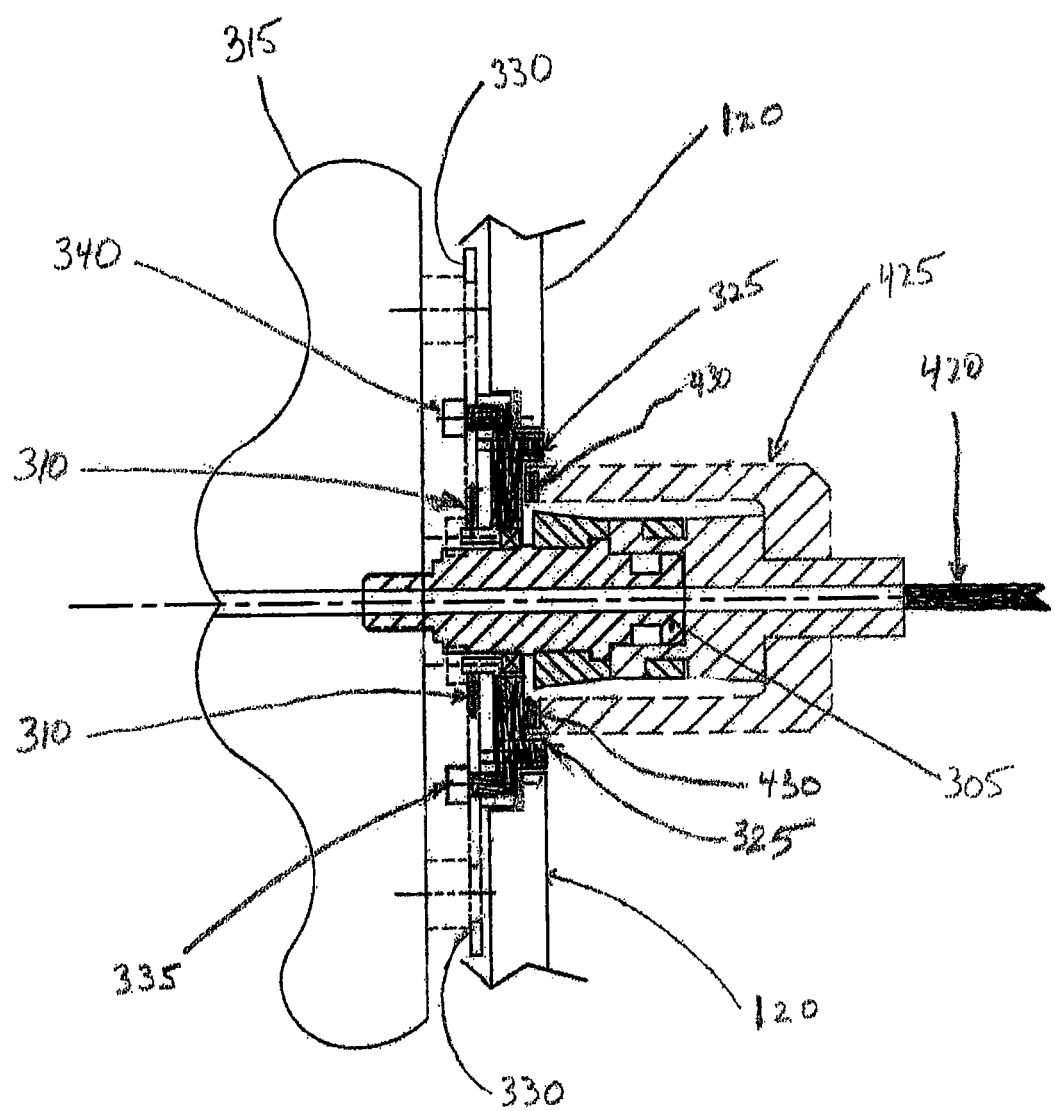
FIG. 6 is an exploded cross-section view of a connector and illumination ring on the front panel of a surgical machine with an RFID illumination ring system as coupled to a connector on a tool for use with a surgical machine with an RFID illumination ring system according to an embodiment of the present invention.

FIG. 6 is an exploded cross-section view of male connector and illumination ring on the front panel of a surgical machine as coupled to a connector on a tool. In FIG. 6, male connector 305 is mounted in manifold 315 of surgical machine 100. Manifold 315 is located behind and attached to front panel 120 of surgical machine 100. Printed circuit board (PCB) 330 is located between manifold 315 and front panel 120. Male connector protrudes through PCB 330 and front panel 120 to allow connection with a female connector on a tool (not shown). Light emitting diodes (LEDs) 335 and 340 are mounted on the side of PCB 330 that faces the manifold 315. In other words, LEDs 335 and 340 are mounted on the side of PCB 330 that does not face front panel 120. RFID reader antenna 310 is also located on or integrated into PCB 330. Lens 325 is located in front of PCB 330 and in a plane substantially parallel with front panel 120. The front face of lens 325 is visible when looking at the front panel 120.

Female connector 425 includes a cable 420 and an RFID tag 430. The cable 420 extends from the connector 425 and toward the hand piece (not shown). RFID tag 430 is located on a front face of female connector 425. As shown, female connector 425 is coupled to male connector 405. In this configuration, a tool is connected to the surgical machine.

When female connector 425 is connected to male connector 405, RFID tag 430 is located close to reader antenna 310. This allows reader antenna 310 and RFID tag 430 to easily communicate with each other. Reader antenna 310 emits an RF field (not shown). When female connector 425 with RFID tag 430 is brought within this field, communication is established between RFID tag 430 and reader antenna 310. It is not necessary that female connector 425 and male connector 305 actually be coupled together for communication to take place. It is only necessary that RFID tag 430 be brought into the RF field emitted from reader antenna 310.

Figure 7:
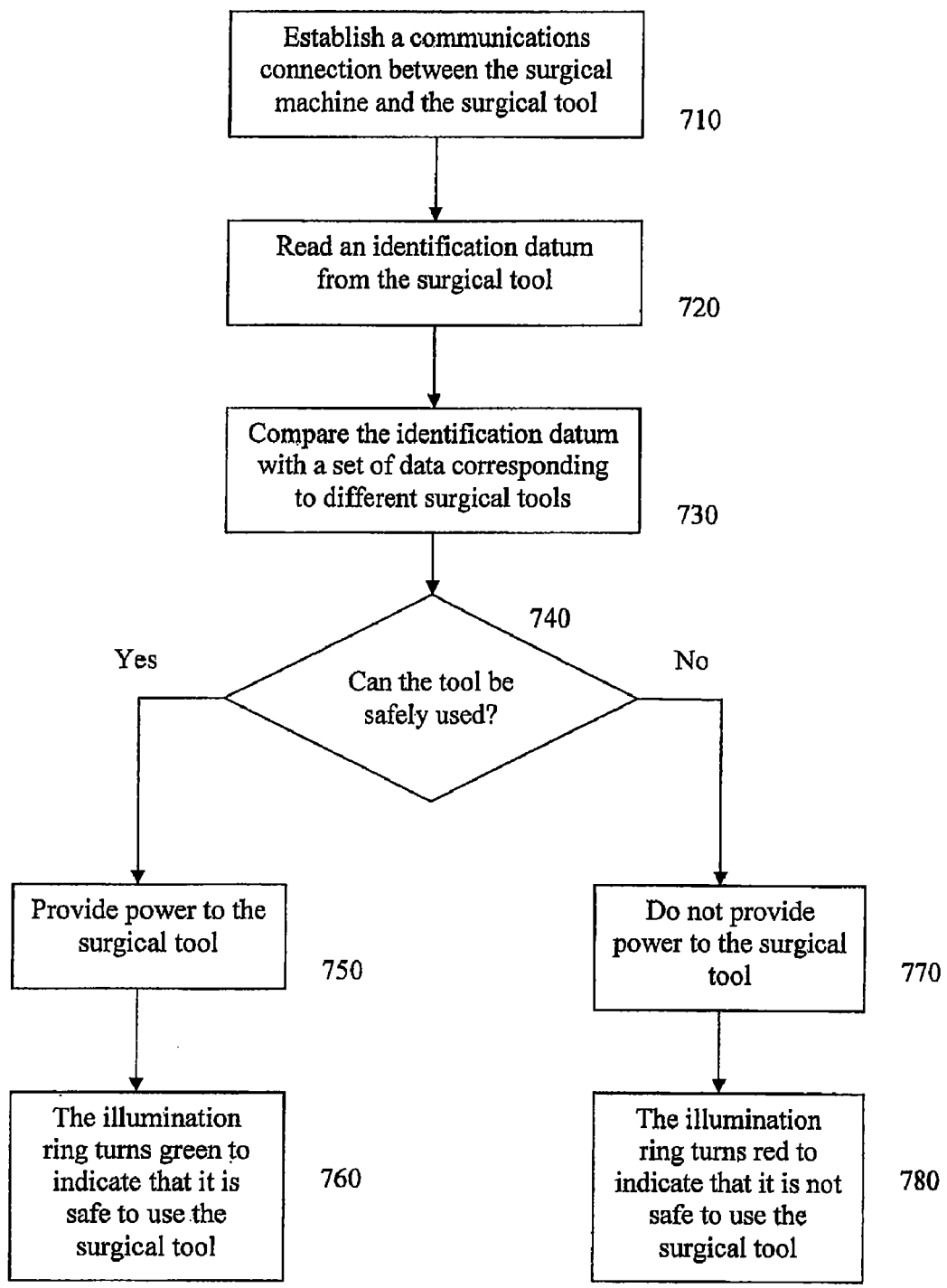
FIG. 7 is a flow chart depicting the smart connector system in one mode of operation consistent with the principles of the present invention.

FIG. 7 is a flow chart depicting the smart connector system of the present invention in one mode of operation. In step 710, a radio frequency communications connection is established between the surgical machine 100 and tool 400. After this communications connection is established, surgical machine 100 via an RFID reader reads an identification datum from tool 400 in step 720. This identification datum can be, for example, a serial number, product identification number, UPC number, or other information that identifies tool 400. In addition, each tool may be provided with a unique serial number or other identifier that can be used to identify the particular tool being connected to the surgical machine 100.

In step 730, the surgical machine 100, or circuitry contained therein, compares the identification datum with a set of data corresponding to different surgical tools. In one case, the surgical machine 100 may have a set of data that indicates all of the different types of tools that can be used with surgical machine 100. For example, the set of data may contain identifiers, such as product codes, for the various types of scissors, probes, lasers, illuminators, hand pieces, consumables, and other types of tools that can be connected to and used with surgical machine 100. In another case, the set of data may contain unique identifiers so that an individual tool can be identified. This set of data may be pre-loaded onto surgical machine 100 or it may be stored on the machine at a later date. The set of data may also be built dynamically so that the surgical machine 100 adds an identifier when a tool 400 is connected. In this manner, the surgical machine may add to the set of data information, such as the unique identifier for a particular tool, the number of times the tool has been connected to surgical machine 100, and various other parameters about the condition and operation of the tool.

In step 740, a decision is made by the surgical machine 100, or the circuitry therein, about whether or not the tool 400 can be used safely. This decision step can involve, for example, determining whether the tool associated the identification datum is proper for a given surgical procedure. If it is proper, then the surgical machine 100 provides power to the surgical tool in step 750. In step 760, the illumination ring turns green to indicate that it is safe to use the tool. If the tool is not proper for the surgical procedure, the surgical machine does not provide power to the tool in step 770. In step 780, the illumination ring turns red to indicate that it is not safe to use the tool.

In this example, the illumination rings 135, 145 display two colors—green and red. In other implementations, the illumination rings 135, 145 can display different colors associated with different states or modes. For example, green could indicate that it is safe to connect the tool, while red could indicate that a connected tool is being powered and cannot be removed. A flashing yellow could indicate that the connected tool has malfunctioned. In this manner, the color displayed can mean different things. Different colors can be used for proper connections, improper connections, tool in use, tool not in use, tool malfunction, tool battery low, or tool needs service.

Figure 8:
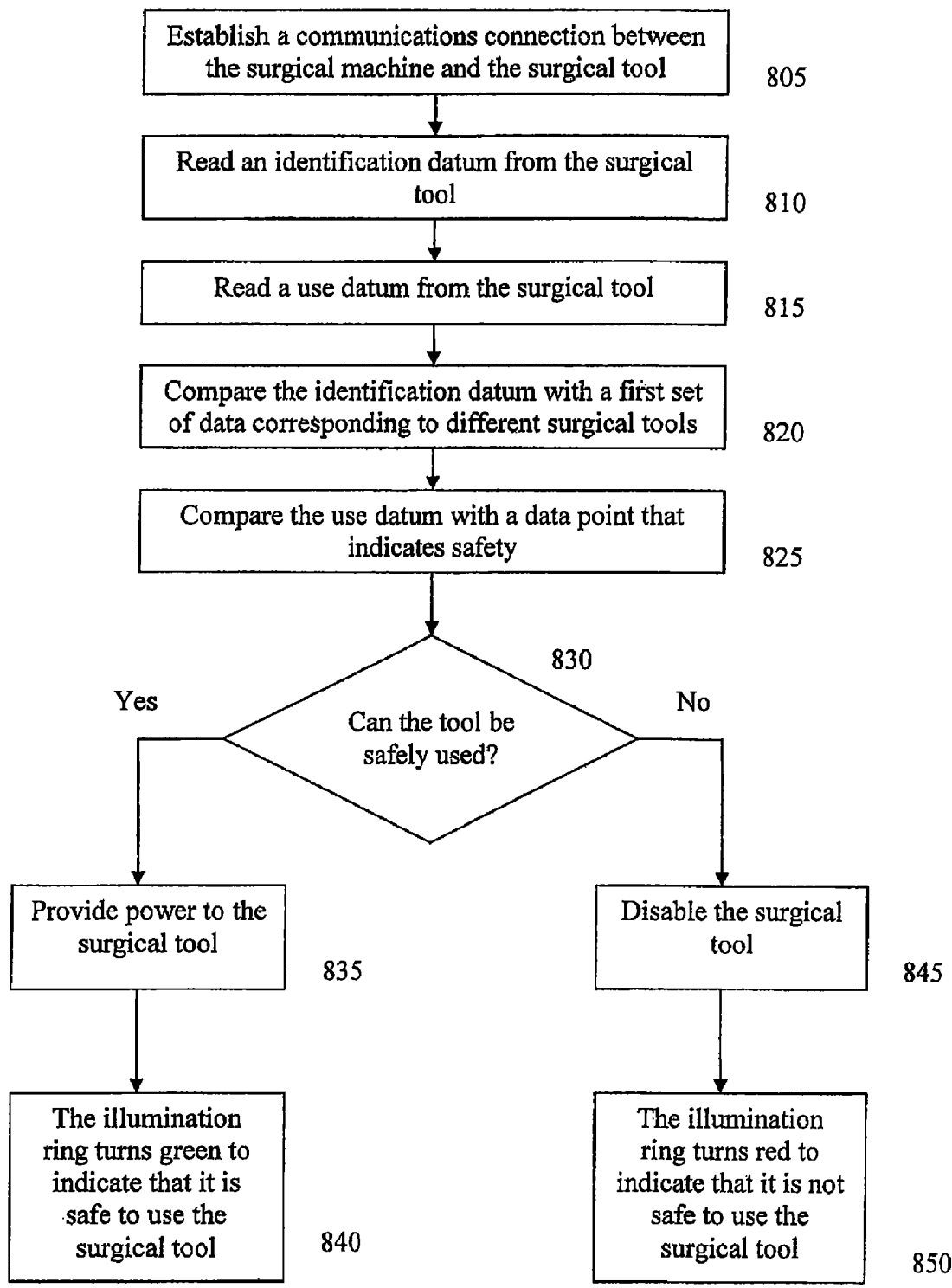
FIG. 8 is a flow chart depicting the smart connector system in another mode of operation consistent with the principles of the present invention.

FIG. 8 is a flow chart depicting the smart connector system of the present invention in another mode of operation. In step 805, a radio frequency communications connection is established between the surgical machine 100 and tool 400. After this communications connection is established, surgical machine 100 via an RFID reader reads an identification datum from tool 400 in step 810. This identification datum can be, for example, a serial number, product identification number, UPC number, or other information that identifies tool 400. In addition, each tool may be provided with a unique serial number or other identifier that can be used to identify the particular tool being connected to the surgical machine 100.

In step 815, surgical machine 100 via an RFID reader reads a use datum from tool 400. This use data may include the number of times the tool has been used, the operating characteristics or parameters of the tool, faults or problems that the tool has, or any other information related to the status, functionality, or operation of the tool 400.

In step 820, the surgical machine 100, or circuitry contained therein, compares the identification datum with a set of data corresponding to different surgical tools. In one case, the surgical machine 100 may have a set of data that indicates all of the different types of tools that can be used with surgical machine 100. For example, the set of data may contain identifiers, such as product codes, for the various types of scissors, probes, lasers, illuminators, hand pieces, consumables, and other types of tools that can be connected to and used with surgical machine 100. In another case, the set of data may contain unique identifiers so that an individual tool can be identified. This set of data may be pre-loaded onto surgical machine 100 or it may be stored on the machine at a later date. The set of data may also be built dynamically so that the surgical machine 100 adds an identifier when a tool 400 is connected.

In step 825, the surgical machine 100, or circuitry contained therein, compares the use datum with a set of data corresponding to acceptable use parameters. In one case, the surgical machine 100 may have a set of data that indicates all of the acceptable uses for tool 400. For example, the set of data may contain use cases for the various types of scissors, probes, lasers, illuminators, hand pieces, consumables, and other types of tools that can be connected to and used with surgical machine 100. This set of data may be pre-loaded onto surgical machine 100 or it may be stored on the machine at a later date. The set of data may also be built dynamically so that the surgical machine 100 adds an identifier or use case when a tool 400 is connected. In this manner, the surgical machine may add to the set of data information, such as the unique identifier for a particular tool, the number of times the tool has been connected to surgical machine 100, and various other parameters about the condition and operation of the tool.

In step 830, a decision is made by the surgical machine 100, or the circuitry therein, about whether or not the tool 400 can be used safely. This decision step can involve, for example, determining whether the tool associated the identification datum is proper for a given surgical procedure. If it is proper, then the surgical machine 100 provides power to the surgical tool in step 835. In step 840, the illumination ring turns green to indicate that it is safe to use the tool. If the tool is not proper for the surgical procedure, the surgical machine disables the tool in step 845. In step 850, the illumination ring turns red to indicate that it is not safe to use the tool.

The decision in step 830 may also be based on the use datum. In this manner, if the use datum is outside a safe range, then the surgical machine disables the tool in step 845. For example, the use datum may indicate that the tool has exceeded the maximum number of safe times that it can be used. In such a case, the surgical machine disables the surgical tool in step 845 and notifies the surgeon of the problem on display 105. In another case, the use datum may indicate a problem with or fault in the tool. In such a case, the surgical machine disables the surgical tool in step 845 and notifies the surgeon of the problem on display 105. Numerous other similar scenarios can be implemented in accordance with the present invention.

In another case, surgical machine 100 may use the use datum to ensure proper operation of the tool. For example, the use datum might include parameters about the specific operating characteristics of the tool 400 that surgical machine 100 can use to fine tune or calibrate tool 400. In this manner, surgical machine 100 reads the use datum and compensates or calibrates the operation of tool 400 based on this use datum.

Figure 9:
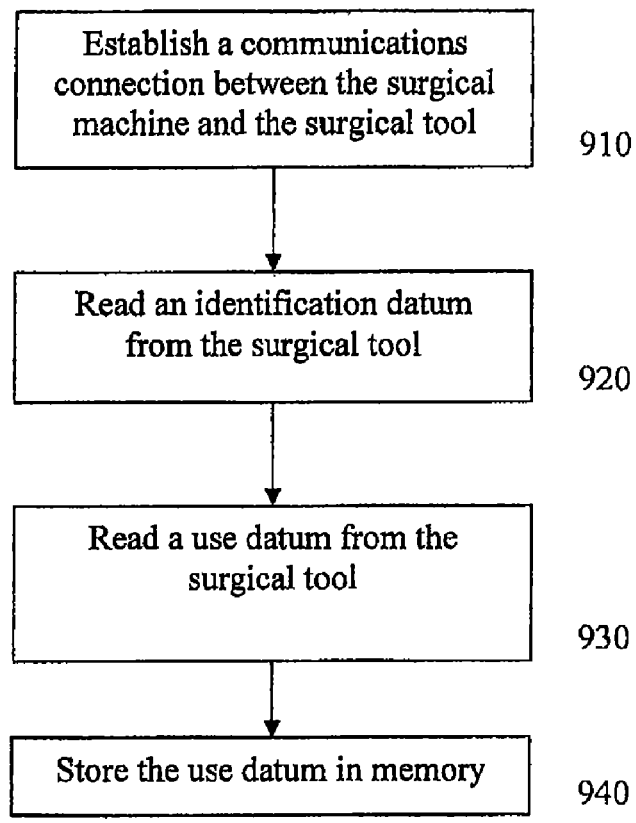
FIG. 9 is a flow chart depicting the smart connector system in another mode of operation consistent with the principles of the present invention.

FIG. 9 is a flow chart depicting the smart connector system of the present invention in another mode of operation. In step 910, a radio frequency communications connection is established between the surgical machine 100 and tool 400. After this communications connection is established, surgical machine 100 via an RFID reader reads an identification datum from tool 400 in step 920. This identification datum can be, for example, a serial number, product identification number, UPC number, or other information that identifies tool 400. In addition, each tool may be provided with a unique serial number or other identifier that can be used to identify the particular tool being connected to the surgical machine 100.

In step 930, surgical machine 100 via an RFID reader reads a use datum from tool 400. This use data may include the number of times the tool has been used, the operating characteristics or parameters of the tool, faults or problems that the tool has, or any other information related to the status, functionality, or operation of the tool 400.

In step 940, the use datum is stored in memory. Alternatively, both the identification datum and the use datum may be stored. The memory may reside in the surgical machine 100. The same data may also be stored on memory contained in the tool itself. In this manner, a set of data related to a specific tool or a class of tools can be built up and stored for future use. Trends in tool usage can be tracked which can provide valuable information to surgeons and medical device manufacturers. For example, detailed surgeon preferences can be extracted from the data. While stored in memory resident on the surgical machine itself, such data could be transmitted via a wired or wireless connection thus enabling a more dynamic use of the data.

From the above, it may be appreciated that the present invention provides an improved RFID illumination ring system for use on a surgical machine. The present invention helps to prevent surgeon error by utilizing RFID to determine if the proper tool is connected to the surgical machine. In addition, the RFID system allows for the collection of useful data. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical machine, comprising:
a machine connector disposed on a face of the surgical machine;
an RFID reader antenna, located in close proximity to the machine connector, and configured to establish a communications connection between the surgical machine and a surgical tool, wherein the RFID reader antenna is configured to read an identification datum from an RFID tag antenna on the surgical tool, wherein the surgical machine is configured to determine if the surgical tool can safely be used with the surgical machine based on the identification datum; and
an illumination ring located on the face of the surgical machine at least partially on a periphery of the machine connector, wherein the surgical machine is configured to illuminate the illumination ring in different colors to indicate different modes of operation or statuses of the surgical machine;
wherein the surgical machine is configured to provide power to the surgical tool only if the determination is made that the surgical tool can safely be used with the surgical machine and wherein illuminating the illumination ring in different colors to indicate different modes of operation or statuses of the surgical machine comprises illuminating the illumination ring in a pattern or color indicative of the determination as to whether the surgical tool can safely be used with the surgical machine.

2. The surgical machine of claim 1 wherein in determining if the surgical tool can safely be used with the surgical machine, the surgical machine is configured to compare the identification datum with a set of data corresponding to different surgical tools.

3. The surgical machine of claim 1, wherein the machine connector is one of at least two machine connectors on the face of the surgical machine and wherein each of at least two of the machine connectors includes a separate illumination ring on a respective periphery of the machine connector.

4. The surgical machine of claim 3, wherein the separate illumination rings are configured to be separately illuminated in a color or pattern indicative of a mode of operation or status of the respective illumination ring's machine connector.

5. The surgical machine of claim 1,
wherein the machine connector is mounted to a manifold located behind and attached to a front panel of the surgical machine;
wherein the surgical machine further comprises a printed circuit board (PCB) located between the manifold and the front panel such that the machine connector protrudes through the PCB and front panel.

6. The surgical machine of claim 5, further comprising light emitting diodes (LEDs) mounted on the PCB.

7. The surgical machine of claim 6, wherein the LEDs are mounted on a side of the PCB that does not face the front panel and wherein the PCB comprises holes that allow light from the LEDs to pass through the PCB.

8. The surgical machine of claim 6, wherein the illumination ring comprises a lens configured to diffuse and/or refract light from the LEDs.

9. The surgical machine of claim 1, wherein the surgical machine is an ophthalmic surgical machine and wherein the surgical tool a scissor, probe, laser, illuminator, or hand piece.

10. A surgical machine, comprising:
a machine connector disposed on a face of the surgical machine;
an RFID reader antenna, located in close proximity to the machine connector, and configured to establish a communications connection between the surgical machine and a surgical tool, wherein the RFID reader antenna is configured to read an identification datum and a use datum from an RFID tag antenna on the surgical tool, wherein the surgical machine is configured to determine if the surgical tool can safely be used with the surgical machine based on the identification datum and the use datum; and an illumination ring located on the face of the surgical machine at least partially on a periphery of the machine connector, wherein the surgical machine is configured to illuminate the illumination ring in different colors to indicate different modes of operation or statuses of the surgical machine;

wherein the surgical machine is configured to disable the surgical tool if the determination is made that the surgical tool cannot safely be used with the surgical machine and wherein illuminating the illumination ring in different colors to indicate different modes of operation or statuses of the surgical machine comprises illuminating the illumination ring in a pattern or color indicative of the determination as to whether the surgical tool cannot safely be used with the surgical machine.

11. The surgical machine of claim 10 wherein in determining if the surgical tool can safely be used with the surgical machine, the surgical machine is configured to compare the identification datum with a first set of data corresponding to different surgical tools to ascertain which tool is connected to the surgical machine; and compare the use datum with a data point that indicates whether it is safe to use the tool.

12. The surgical machine of claim 10 wherein in determining if the surgical tool can safely be used with the surgical machine, the surgical machine is configured to compare the identification datum with a first set of data corresponding to different surgical tools to ascertain which tool is connected to the surgical machine; and compare the use datum with a data point that indicates a number of times the tool can be used safely.

13. The surgical machine of claim 10 wherein the use datum provides information about a problem with the surgical tool.

14. The surgical machine of claim 10, wherein the machine connector is one of at least two machine connectors on the face of the surgical machine and wherein each of at least two of the machine connectors includes a separate illumination ring on a respective periphery of the machine connector.

15. The surgical machine of claim 14, wherein the separate illumination rings are configured to be separately illuminated in a color or pattern indicative of a mode of operation or status of the respective illumination ring's machine connector.

16. The surgical machine of claim 10,
wherein the machine connector is mounted to a manifold located behind and attached to a front panel of the surgical machine;
wherein the surgical machine further comprises a printed circuit board (PCB) located between the manifold and the front panel such that the machine connector protrudes through the PCB and front panel.

17. The surgical machine of claim 16, further comprising light emitting diodes (LEDs) mounted on the PCB.

18. The surgical machine of claim 17, wherein the LEDs are mounted on a side of the PCB that does not face the front panel and wherein the PCB comprises holes that allow light from the LEDs to pass through the PCB.

19. The surgical machine of claim 17, wherein the illumination ring comprises a lens configured to diffuse and/or refract light from the LEDs.

20. The surgical machine of claim 10, wherein the surgical machine is an ophthalmic surgical machine and wherein the surgical tool a scissor, probe, laser, illuminator, or hand piece.

\* \* \* \* \*